United States Patent
Masui et al.

(10) Patent No.: US 6,987,187 B2
(45) Date of Patent: Jan. 17, 2006

(54) PROCESS FOR PREPARATION OF AMIDINE DERIVATIVES

(75) Inventors: Toshiaki Masui, Amagasaki (JP);
Kyozo Kawata, Hirakata (JP);
Takayuki Kasai, Amagasaki (JP);
Makoto Kakinuma, Amagasaki (JP)

(73) Assignee: Shionogi & Co., Ltd., Osaka-fu (JP)

( * ) Notice: Subject to any disclaimer, the term of this patent is extended or adjusted under 35 U.S.C. 154(b) by 16 days.

(21) Appl. No.: 10/483,771

(22) PCT Filed: Jul. 15, 2002

(86) PCT No.: PCT/JP02/07142

§ 371 (c)(1),
(2), (4) Date: Jan. 14, 2004

(87) PCT Pub. No.: WO03/008421

PCT Pub. Date: Jan. 30, 2003

(65) Prior Publication Data

US 2004/0167157 A1    Aug. 26, 2004

(30) Foreign Application Priority Data

Jul. 16, 2001    (JP) ............................. 2001-215361

(51) Int. Cl.
C07D 471/00    (2006.01)
C07D 215/38    (2006.01)
C07D 215/18    (2006.01)

(52) U.S. Cl. .................. 546/82; 546/89; 546/153; 546/159; 546/160

(58) Field of Classification Search ................ 546/180, 546/153, 159, 82, 89
See application file for complete search history.

(56) References Cited

U.S. PATENT DOCUMENTS 5,461,062 A    10/1995    Takada et al. ............... 514/293

FOREIGN PATENT DOCUMENTS

| EP | 556008 | 8/1993 |
|----|--------|--------|
| EP | 1 270 578 | 1/2003 |
| PL | 0157443 | 5/1992 |
| WO | 01/74821 | 10/2001 |

OTHER PUBLICATIONS

Volovenko et al, Chem. Abs. vol. 117 No. 233799, "Synthesis and biological activity of alpha sub. 2-pyridylacetonitirl;es" (1992) (Best Available).*

M. Adachi et al., "Intermolecular transfer of an alkenyl group in enamines: application to synthesis of [b]-fused pyridins", Tetrahedron Letters, 1996, vol. 37, No. 49, pp. 8871-8874.

M. Dolezal et al., "Synthesis and antimycobacterial, antigungal, and photosynthesis-inhibiting evaluation of some anilides of substituted pyrazine-2-carboxylic acids", Chemical Papers, 2000, vol. 54, No. 4, pp. 245-248.

M. Adachi et al., "Intermolecular transfer of an alkenyl group in enamines: application to synthesis of [b]-fused pyridins", Tetrahedron Letters, 1996, vol. 37, No. 49, pp. 8871-8874.

M. Dolezal et al., "Synthesis and antimycobacterial, antigungal, and photosynthesis-inhibiting evaluation of some anilides of substituted pyrazine-2-carboxylic acids", Chemical Papers, 2000, vol. 54, No. 4, pp. 245-248.

* cited by examiner

Primary Examiner—Rita Desai
Assistant Examiner—Raymond Covington
(74) Attorney, Agent, or Firm—Wenderoth, Lind & Ponack, L.L.P.

(57) ABSTRACT

A process for producing amidine derivatives represented by the following reaction scheme, characterized in that the reactions of steps 1 and 3 are conducted in acetonitrile and the reaction of step 2 is conducted in acetone.

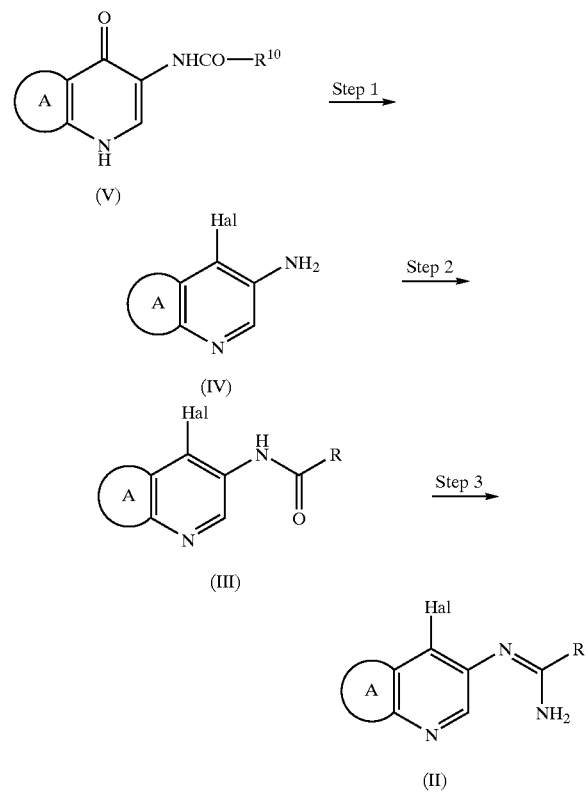

7 Claims, No Drawings

PROCESS FOR PREPARATION OF AMIDINE DERIVATIVES

This application is a U.S. national stage of International Application No. PCT/JP02/07142 filed Jul. 15, 2002.

TECHNICAL FIELD

The present invention relates to a novel process for producing amidine derivatives, which are intermediates of condensed imidazopyridine derivatives that are useful for pharmaceuticals.

BACKGROUND ART

JP 1993/286973A discloses a process for producing condensed imidazopyridine derivatives which are useful as a psychotropic drug:

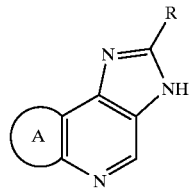
(I)

wherein,
R represents optionally substituted aryl or optionally substituted aromatic heterocyclic group;
ring A represents a 5 to 9 membered alicyclic group, which may comprise at least one of O, S, SO, $SO_2$ and/or $NR^1$ and may be substituted with at least one alkyl;
$R^1$ represents hydrogen, alkyl, esterified carboxyl, carbamoyl or an acyl. Also, amidine derivatives of the formula:

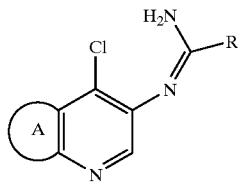

wherein R and ring A are each as defined above, are disclosed therein as an intermediate thereof.

The Japanese patent publication discloses the process for producing said amidine derivatives wherein methylene chloride is used as a reaction solvent:

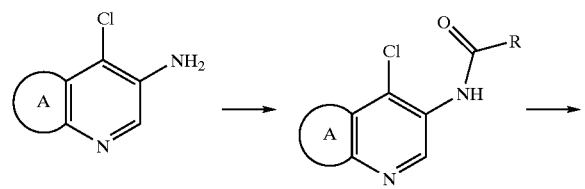

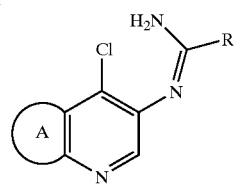

wherein R and ring A are each as defined above. For preparation of the starting material of said process, the following reaction is disclosed therein:

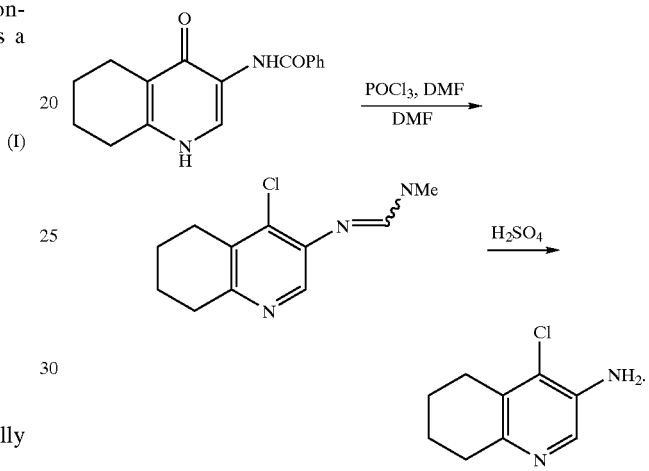

In this reaction, a pyridone amide is reacted with phosphorus oxychloride in dimethylformamide (DMF), and the resultant product is hydrolyzed using sulfuric acid to obtain a corresponding amine.

Tetrahedron Letters, Vol.37, No.49, pp. 8871–8874, 1996 discloses similar reaction for preparing of a compound, which is one of the condensed imidazopyridine derivatives of the formula I and particularly useful for senile dementia. However, the reaction disclosed is different from that in the above Japanese patent publication in that a pyridone amide is reacted in methylene chloride to obtain a corresponding amine.

Heretofore, the above amidine derivatives, which are intermediates of the condensed imidazopyridine derivatives of the formula (I), have been prepared by the reaction in methylene chloride or dimethylformamide. However, these conventional processes afford by-products in a high yield and show slowed progress of the reaction because of side reactions. Furthermore, methylene chloride requires equipments for recovery because it is under emission control globally. Additionally, dimethylformamide is difficult to evaporate to remove because of its high boiling point (153° C.), and therefore, the procedures to remove the impurities and isolate the desired product would become complicated. Thus, these conventional processes require these complicated reaction operation and were not sufficiently practical in industrial productions from the viewpoint of productivity. Therefore, there is need for convenient and efficient process for producing the above amidine derivatives, which are the intermediates of the condensed imidazopyridine derivatives of the formula (I).

DISCLOSURE OF INVENTION

The present invention provides a novel process useful in an industrial production of amidine derivatives, which are intermediates of condensed imidazopyridine derivatives that are useful for pharmaceuticals.

The present invention provides a process for producing a compound of the formula (II):

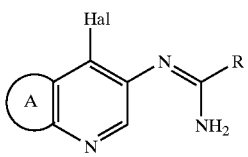

(II)

wherein
  ring A represents a 5 to 9 membered alicyclic group, which may contain at least one of O, S, SO, SO$_2$ and/or NR$^1$ and may be substituted with at least one alkyl;
  R$^1$ is hydrogen, alkyl, esterified carboxy, carbamoyl or acyl;
  R is optionally substituted aryl or optionally substituted aromatic heterocyclic group; and
  Hal is a halogen, comprising
  Step 1, wherein a compound of the formula (V):

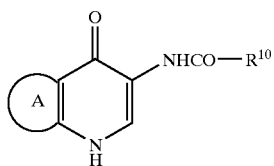

(V)

wherein
  R$^{10}$ is optionally substituted aryl, optionally substituted aromatic heterocyclic group, optionally substituted alkyl, or optionally substituted cycloalkyl; and ring A is as defined above, is reacted with a halogenating agent in acetonitrile in the presence of dimethylformamide and then hydrolyzed to obtain a compound of the formula (IV):

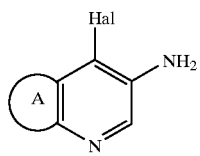

(IV)

wherein ring A is as defined above, and Hal is halogen,
  Step 2, wherein the resultant compound (IV) is reacted with a compound of the formula R-COR$^{11}$, wherein R is optionally substituted aryl or optionally substituted aromatic heterocyclic group, and R$^{11}$ is hydroxy or halogen, in acetone in the presence of an organic base and optionally further a halogenating agent to obtain a compound of the formula (III):

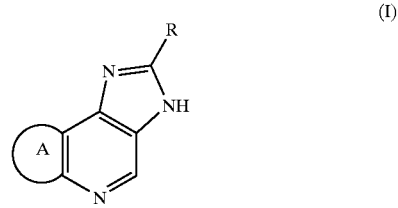

(III)

wherein ring A, Hal and R are as defined above, and
  Step 3, wherein the obtained compound of the formula (III) is reacted with a halogenating agent in acetonitrile in the presence of an organic base and then aminated.

Also, the present invention provides a process for producing a condensed imidazopyridine derivatives of the formula (I):

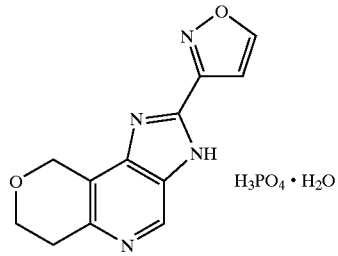

(I)

wherein ring A and R are as defined above, comprising that the compound of the formula (II) obtained in the above process is reacted in the presence of a sulfinate.

Further, the present invention provides a process for producing a crystal of 2-(3-isoxazolyl)-3,6,7,9-tetrahydroimidazo[4,5-d]pyrano[4,3-b]pyridine phosphate monohydrate of the formula (Ia):

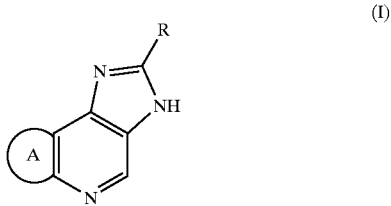

(Ia)

comprising that a compound of the formula (I):

(I)

wherein R is 3-isoxazolyl, and ring A is

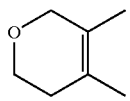

is treated with an aqueous solvent containing phosphoric acid, and the obtained phosphate is crystallized according to conventional procedure.

The terms used herein are defined as below.

The term "alkyl" includes a straight or branched alkyl having 1 to 10 carbon atoms. For example, methyl, ethyl, n-propyl, isopropyl, n-butyl, isobutyl, sec-butyl, tert-butyl, n-pentyl, isopentyl, neopentyl, tert-pentyl, 2-methylbutyl, n-hexyl, isohexyl, heptyl, isoheptyl, octyl, isooctyl, nonyl, decyl and the like are included. Alkyl having 1 to 6 carbon atoms is preferred.

For "optionally substituted alkyl", substituent includes alkyl, hydroxy, alkoxy, aryloxy, acyloxy, carboxy, ester such as alkoxycarbonyl and aralkoxycarbonyl, cyano, amino, mono- or di-substituted amino, hydrazino, hydroxyamino, halogen, nitro, acyl, carbamoyl, thiocarbamoyl, carbamoyloxy, thiocarbamoyloxy, ureido, thioureido, sulfonamide, mono- or di-substituted sulfonamide, sulfonic acid, halogenoalkyl, hydroxyalkyl, alkoxyalkyl, acyloxyalkyl, nitroalkyl, aminoalkyl, acylaminoalkyl, cyanoalkyl, carboxyalkyl and the like.

The term "esterified carboxy" includes alkoxycarbonyl, aryloxycarbonyl, aralkoxycarbonyl and the like. The examples are methoxycarbonyl, ethoxycarbonyl, tert-butoxycarbonyl, benzyloxycarbonyl and the like.

The term "acyl" includes an aliphatic acyl having 1 to 10 carbon atoms and an aromatic acyl. The examples are formyl, acetyl, propionyl, butyryl, isobutyryl, valeryl, pivaloyl, hexanoyl, acryloyl, propioloyl, methacryloyl, crotonoyl, cyclohexanecarbonyl, benzoyl, 4-nitrobenzoyl, 4-tert-butylbenzoyl, benzenesulfonyl, toluenesulfonyl and the like. "5- to 9-membered alicyclic group" condenses with the neighboring pyridine ring and includes specifically a cyclopenteno ring, a cyclohexeno ring, a cyclohepteno ring, a cyclooteno ring, and a cyclononeno ring, and a 5- to 7-membered alicyclic group is preferred. Also, said alicyclic group may contain at least one of O, S, SO, SO$_2$ and/or NR$^1$ wherein R$^1$ is as defined above, and includes pyrrolidino, pyrrolino, imidazolidino, imidazolino, pyrazolidino, dihydrothiopheno, dihydrofurano, thiazolino, dihydropyrano, dihydrothiopyrano, piperidino, piperazino, morpholino, thiomorpholino, tetrahydropyridino, and tetrahydropyrimidino and the like. Dihydropyrano, dihydrothiopyrano and piperidino is particularly preferable. These rings may be substituted with alkyl, which is preferably one or two methyl or ethyl.

The term "aryl" includes phenyl, naphthyl, anthryl, indenyl, phenanthryl and the like.

The term "optionally substituted aryl" includes the above mentioned "aryl" which may have at one or more of possible positions one or more of substituents selected from alkyl, hydroxy, alkoxy, aryloxy, acyloxy, carboxy, ester such as alkoxycarbonyl and aralkoxycarbonyl, cyano, amino, mono- or di-substituted amino, hydrazino, hydroxyamino, halogen, nitro, acyl, carbamoyl, thiocarbamoyl, carbamoyloxy, thiocarbamoyloxy, ureido, thioureido, sulfonamide, mono- or di-substituted sulfonamide, sulfonic acid, halogenoalkyl, hydroxyalkyl, alkoxyalkyl, acyloxyalkyl, nitroalkyl, aminoalkyl, acylaminoalkyl, cyanoalkyl, carboxyalkyl and the like. Preferable example includes a substituted or an unsubstituted phenyl, and the example of a substituent for such phenyl includes methyl, methoxy, chloro and the like.

The aryl moiety of "aryloxy", "aryloxycarbonyl" and "aralkoxycarbonyl" are the same as that of the above "aryl".

The alkyl moiety of "halogenoalkyl", "hydroxyalkyl", "alkoxyalkyl", "acyloxyalkyl", "nitroalkyl", "aminoalkyl", "acylaminoalkyl", "cyanoalkyl" and "carboxyalkyl" are the same as that of the above "alkyl".

The term "aromatic heterocyclic group" means a cyclic group containing one or more of hetero atoms optionally selected from O, S and N in the ring, and said cyclic group may condense with a carbocycle or another heterocycle. The examples are 5- to 6-membered aromatic heterocyclic groups such as pyrrolyl, imidazolyl, pyrazolyl, pyridyl, pyridazinyl, pyrimidinyl, pyrazinyl, triazinyl, isoxazolyl, oxazolyl, oxadiazolyl, isothiazolyl, thiazolyl, thiadiazolyl, furyl, thienyl and the like, and condensed aromatic heterocyclic groups such as indolyl, benzimidazolyl, indazolyl, indolizinyl, quinolyl, isoquinolyl, cinnolinyl, phthalazinyl, quinazolinyl, naphthyridinyl, quinoxalinyl, pteridinyl, benzisoxazolyl, benzoxazolyl, oxadiazolyl, benzoxadiazolyl, benzisothiazolyl, benzothiazolyl, benzothiadiazolyl, benzofuryl, benzothienyl, carbazolyl, phenazinyl and the like.

For "optionally substituted aromatic heterocyclic group" substituent includes alkyl, hydroxy, alkoxy, carboxy, ester such as alkoxycarbonyl and aralkoxycarbonyl, cyano, amino, mono- or di-substituted amino, hydrazino, hydroxyamino, halogen, nitro, acyl, carbamoyl, thiocarbamoyl, carbamoyloxy, thiocarbamoyloxy, ureido, thioureido, sulfonamide, mono- or di-substituted sulfonamide, sulfonic acid, halogenoalkyl, hydroxyalkyl, alkoxyalkyl, acyloxyalkyl, nitroalkyl, aminoalkyl, acylaminoalkyl, cyanoalkyl, carboxyalkyl and the like. Although said optionally substituted aromatic heterocyclic group may be substituted at one or more of possible positions, preferably an unsubstituted 5-membered aromatic heterocyclic group, more preferably unsubstituted thienyl, unsubstituted furyl, unsubstituted isoxazolyl or unsubstituted pyridyl, and most preferably unsubstituted isoxazolyl.

As used herein, "halogen" includes fluorine, chlorine, bromine and iodine. Chlorine is preferable.

The term "cycloalkyl" includes a carbocyclic ring having 3 to 8 carbon atoms, and the examples are cyclopropyl, cyclobutyl, cyclopentyl, cyclohexyl, cycloheptyl, cyclooctyl and the like.

For "optionally substituted cycloalkyl", substituent is the same as exemplified for "optionally substituted alkyl".

The term "alkoxy" includes straight or branched alkoxy having 1 to 10 carbon atoms, and the examples are methoxy, ethoxy, n-propoxy, isopropoxy, n-butoxy, isobutoxy, sec-butoxy, tert-butoxy, n-pentyloxy, isopentyloxy, neopentyloxy, tert-pentyloxy, 2-methylbutoxy, n-hexyloxy, isohexyloxy, heptyloxy, isoheptyloxy, octyloxy, isooctyloxy, nonyloxy, decyloxy and the like. Preferable is a lower alkoxy having 1 to 6 carbon atoms.

The alkoxy moiety of "alkoxycarbonyl", "alkoxyalkyl" and "aralkoxycarbonyl" are the same as that of the above "alkoxy".

The terms "mono- or di-substituted amino" and "mono- or di-substituted sulfonamide" include amino and sulfonamide substituted with one or two of hydroxy, halogen, alkyl, alkenyl, acyl, aryl and the like.

The acyl moiety of "acyloxy", "acylaminoalkyl" and "acyloxyalkyl" are the same as that of the above "acyl".

BEST MODE FOR CARRYING OUT THE INVENTION

The process of the invention for producing an amidine derivative of the formula (II) is summarized in the following scheme:

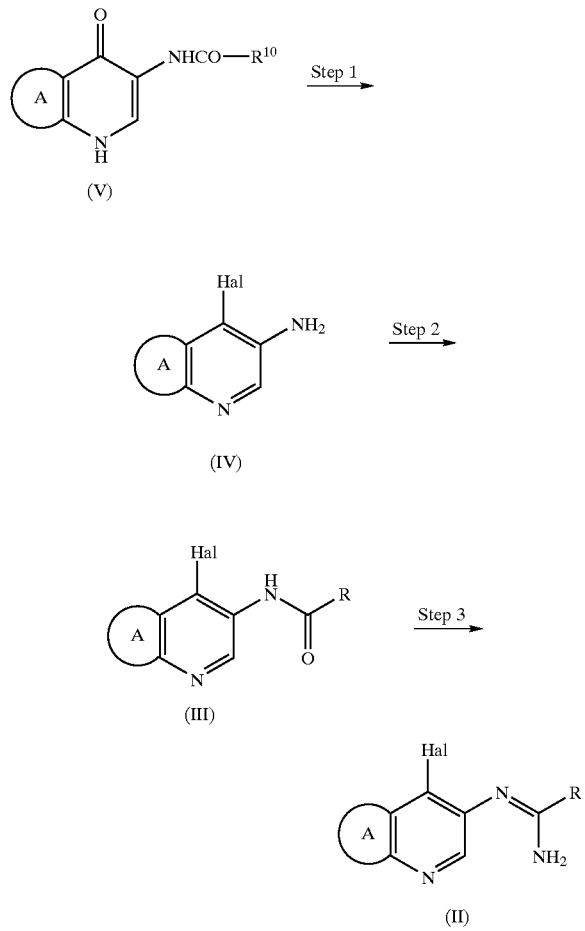

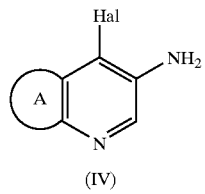

wherein ring A, R, $R^{10}$ and Hal are as defined above.

Detailed description for each step is as follows.

Step 1:

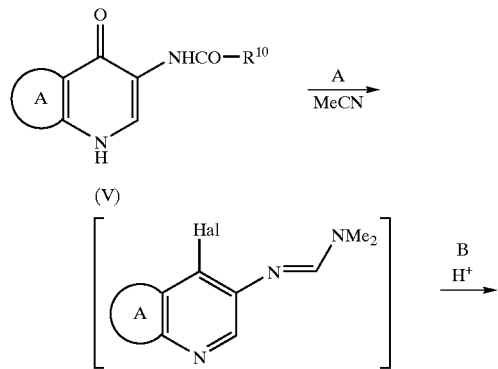

In this step, a compound of the formula (V) is firstly reacted with a halogenating agent in acetonitrile in the presence of dimethylformamide at –20° C. to 100° C., preferably room temperature to 60° C., for several minutes to several hours, preferably 1 to 5 hours (step A). Preferable halogenating agent includes phosgene, thionyl chloride, phosphorus oxychloride and the like. Phosphorus oxychloride is particularly preferable.

Next, the compound obtained in step A is subjected to hydrolysis to afford a compound of the formula (IV) (step B). The hydrolysis is preferably conducted at 0° C. to under heating, preferably room temperature to 80° C., for several minutes to several hours, preferably 10 minutes to 5 hours, using hydrochloric acid, phosphoric acid, sulfuric acid or the like. Preferable solvent includes ethyl acetate, water and the like. Water is particularly preferable.

In step A, an oxazole compound can be formed as a by-product. As the result of the hydrolysis reaction in step B, the oxazole compound is reversed to the compound (V), which results in precipitation. In the conventional processes, such precipitated materials, which can bring about obstacles to the operations in the process, had to be removed by filtration. In the above step of the invention, wherein it is conducted in acetonitrile, an oxazole compound is less formed and not required to be removed by filtration. Accordingly, the above step allows efficient production of the compound (IV).

Step 2

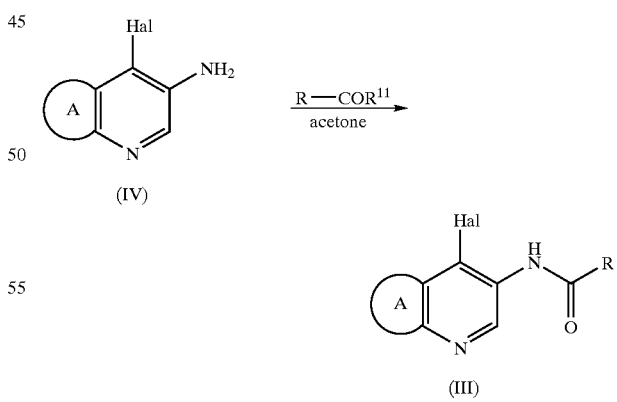

In this step, the compound (IV) is reacted with the compound of the formula R-$COR^{11}$, wherein R is as defined above and $R^{11}$ is hydroxy or halogen, in acetone in the presence of an organic base, optionally further in the presence of a halogenating agent, at –20° C. to under heating, preferably at –10° C. to room temperature, for several minutes to several hours, preferably 1 to 5 hours, and then water is added to afford a crystal of the compound of the formula (III). Examples of the organic base include triethylamine, pyridine and the like. Pyridine is particularly preferable. Examples of halogenating agent include phosgene, thionyl chloride, phosphorus oxychloride and the like. Phosphorus oxychloride is particularly preferable.

This reaction, which is conducted in acetone, can afford the compound (III) efficiently, since it is conducted in a simple manner that all reactants are mixed together to react and water is added to precipitate crystals of the compound (III).

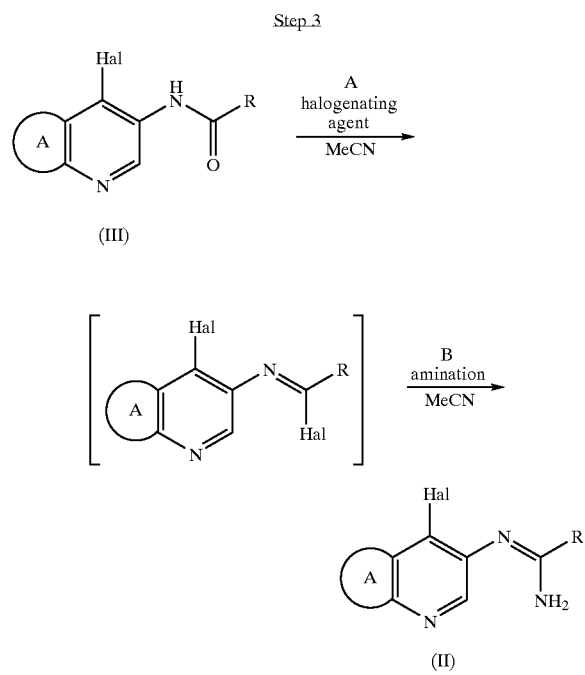

In this step, a compound (III) is reacted with a halogenating agent such as phosgene, thionyl chloride, phosphorus pentachloride and phosphorus oxychloride in acetonitrile in the presence of an organic base such as triethylamine, pyridine or the like, at 0° C. to under heating, preferably at 0° C. to 50° C., for several minutes to several hours, preferably 10 minutes to 5 hours (step A)

The compound obtained in step A is then aminated with ammonia gas, aqueous ammonia or the like (step B). Pyridine is preferable organic base. Phosphorus pentachloride is preferable halogenating agent. The amination is preferably conducted by addition of aqueous ammonia to the reaction mixture.

This reaction, using acetonitrile as a reaction solvent, can afford the compound (II) efficiently, since it does not cause the problem that the solvent and aqueous ammonia are not sufficiently mixed and that progression of amination is thus slowed down.

In another embodiment of the invention, the compound (II), which is obtained in the above reaction, is further reacted in the presence of a sulfinate to afford the compound of the formula (I):

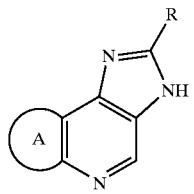

wherein ring A and R are defined above.

Firstly, the compound (II) can be reacted in a suitable solvent, such as dimethylformamide, dimethylsulfoxide, N,N'-dimethyl imidazolidinone, N-methylpyrrolidone, N,N-dimethylacetamide, Dowtherm™ A or the like, in the presence of a sulfinate for several tens of minutes to several hours. As the sulfinate, for example, sodium p-toluenesulfinate, potassium p-toluenesulfinate, lithium p-toluenesulfinate, sodium methanesulfinate, potassium methanesulfinate or lithium methanesulfinate can be used. Reaction temperature would be about 90° C. to about 150° C., preferably about 100° C. to about 145° C. This reaction is preferably conducted in the presence of "acid" or "salt of an organic base", in addition the above sulfinate. For example, methanesulfonic acid, p-toluenesulfonic acid or the like can be used as "acid". Preferable "salt of the organic base" are those which pKb is 5 or less, specifically, hydrochlorides or hydrobromides of pyridine, N-methylmorpholine or N,N-dimethylpyridine and the like, or hydrochlorides, hydrobromides or methanesulfonates of the compound (I) and the like. In the case that the "acid" or the "salt of an organic base" is coexistent with a sulfinate, the reaction may be conducted at about 130° C. or below, preferably about 120° C. or below, more preferably about 100° C. or below. The lower limit of the reaction temperature to drive the reaction preferably would be about 90° C., preferably about 100° C.

The compound of the formula (I) can be converted by the conventional method to a pharmaceutically acceptable salt thereof or solvate thereof. Example of the pharmaceutically acceptable salt of the compound (I) includes salts formed with an inorganic acid such as hydrochloric acid, sulfuric acid, nitric acid, phosphoric acid, hydrofluoric acid, hydrobromic acid; salts formed with an organic acid such as formic acid, acetic acid, tartaric acid, lactic acid, citric acid, fumaric acid, maleic acid, succinic acid, methanesulfonic acid, benzenesulfonic acid, p-toluenesulfonic acid; salts formed with an acidic amino acid such as ornithine, aspartic acid, glutamic acid. Phosphates are particularly preferable. The solvate of the compound (I) or the pharmaceutically acceptable salt thereof includes those in which the compound (I) or the pharmaceutically acceptable salt thereof is coordinated with possible number of molecule of a suitable organic solvent or water. Preferable solvate is a hydrate, more preferably a monohydrate.

Another embodiment of the invention provides a process for preparing 2-(3-isoxazolyl)-3,6,7,9-tetrahydroimidazo[4,5-d]pyrano[4,3-b]pyridine phosphate monohydrate represented by the formula (Ia):

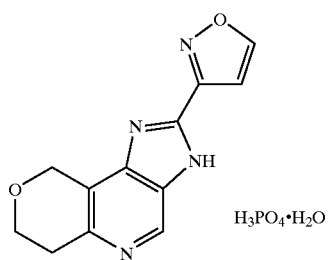

which comprises that the compound of the formula (I) wherein R is 3-isoxazolyl, and ring A is

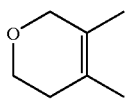

is prepared in the manner as described above, and the resultant product is treated with an aqueous solvent containing phosphoric acid to obtain a phosphate salt thereof, which is then crystallized by the conventional methods. Example for the aqueous solvent containing phosphoric acid is isopropanol containing 20% of water.

At least two kinds of crystal forms, i.e., prism crystals and needle crystals, are found as crystals of the compound (Ia). These crystals are distinguished by characteristic peaks of powder X-ray diffraction or absorption bands of infrared absorption spectrum.

The present invention is further explained by the following Examples, which are not intended to limit the scope of the present invention.

EXAMPLE 1

Synthesis of Compound 3

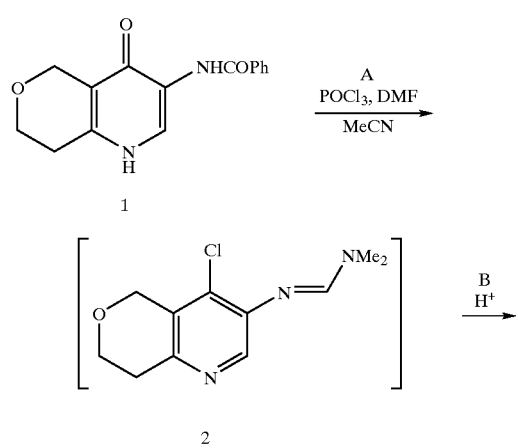

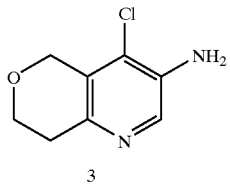

Compound 1 (30.0 g, 0.666 mol) was suspended in 165 mL of acetonitrile, and the suspension was cooled to −10° C. 25.5 g of phosphorus oxychloride in dimethylformamide (40.5 g) was added dropwise to the suspension at −10° C. to −5° C. The mixture was heated to 45±5° C. over about 30 minutes and stirred for about 2 hours. After ice cooling, 180 mL of water was added dropwise to the mixture, the mixture was stirred to dissolve any precipitated material. After heating to 80±5° C., the mixture was stirred for about 1.5 hours with evaporating acetonitrile. The residue was concentrated under reduced pressure to about 15 mL of the volume and then cooled to room temperature. The residue was washed with 150 mL of toluene (or ethyl acetate), and the washing solution was extracted with 30 mL to 60 mL of water. To the obtained aqueous layer, 48% sodium hydroxide aqueous solution was added until pH 4–6, and seed crystals of Compound 3 were then added to crystallize the compound. Further, 48% sodium hydroxide aqueous solution was added portionwise to the aqueous layer until pH 8 and stirred at room temperature for about 1 hour. The resultant crystal of Compound 3 is filtered, washed with 60 mL of water, and dried under reduced pressure (55° C., 5 hours) to obtain Compound 3 (17.49 g, 85.3%).

Oxazole compound, which was formed as by-product in step A, was about 0.1% yield (compared to the intermediate Compound 2). The oxazole compound can be reversed to Compound 1 during the reaction in step B (hydrolysis) and form precipitation thereof, which causes troubles in operations for separation. However, the yield of the oxazole compound in the present process was so small that it did not cause such troubles.

EXAMPLE 2

Synthesis of Compound 4

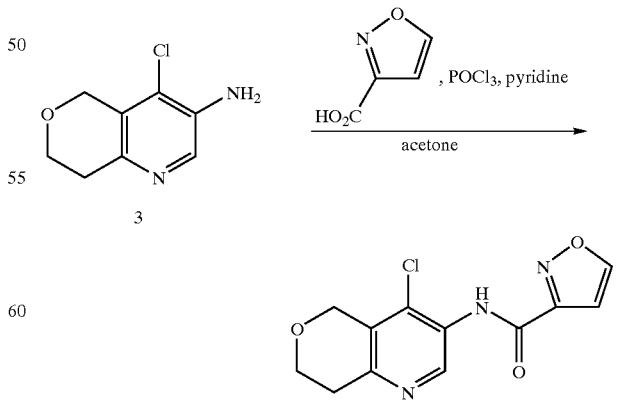

Compound 3 (24.0 g) and 16.17 g of isoxazole-3-carboxylic acid were suspended in 288 mL of acetone, 49.36 g of pyridine was added thereto and the suspension was cooled to −10° C. 31.89 g of phosphorus oxychloride was poured into the suspension to react at 20±10° C. for about 30 minutes. The reaction mixture was cooled to 5° C. or below, 5.3 mL of water was added dropwise to the mixture at 20° C., and 355 mL of water was poured therein. Then, 10% sodium hydroxide aqueous solution was added dropwise to the mixture until pH 4.5, and the mixture was stirred at 15±10° C. for about 2 hours to precipitate crystals. The crystallized slurry obtained was filtered, and the crystals were washed sequentially with 48 mL of 10% aqueous acetone, 192 mL of water, and 72 mL of 10% aqueous acetone, and dried in vacuo to afford Compound 4 (33.24 g, 91.4%).

EXAMPLE 3

Synthesis of Compound 6

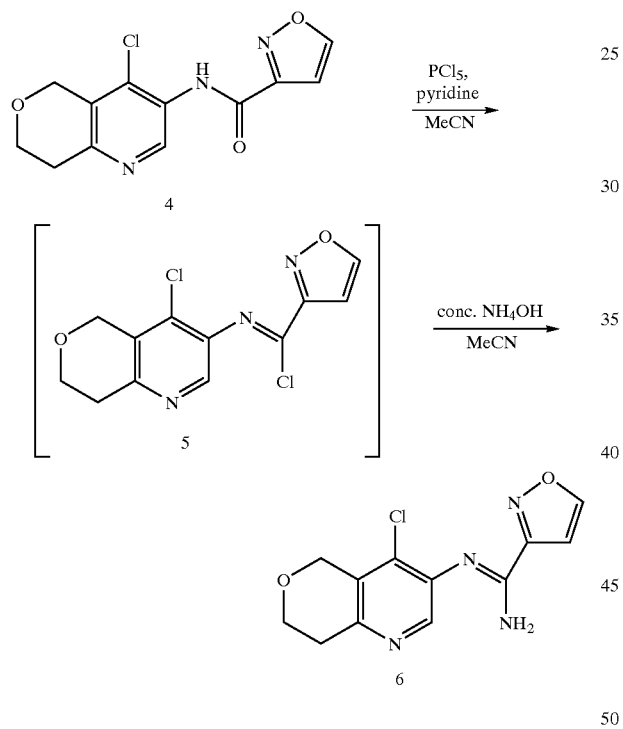

Compound 4 (10.0 g) was suspended in 100 mL of acetonitrile, and the suspension was cooled to 5° C. 10.4 g of phosphorus oxychloride was added to this suspension to react at room temperature for about 1 hour. 3.96 g of pyridine was then poured into the reaction mixture, which is then heated to 45±5° C. to react for about 3 hours. The reaction mixture was cooled to 20° C. and poured into 15% brine (80 g) which was previously cooled to −10° C. After the layers were separated, 100 mL of acetonitrile was added to the aqueous layer, the pH was adjusted to 3 with 10% sodium hydroxide aqueous solution, and the acetonitrile layer was separated. After the acetonitrile layers were combined and the reaction apparatus were washed with 10 mL of acetonitrile to collect residual reactants, 28% aqueous ammonia was added to the mixture to react at 30±5° C. for about 3 hours. The reaction mixture was concentrated to 80 mL under reduced pressure. The residue was cooled to −5° C., stirred for about one hour and then filtrated. The crystal was washed with 30 mL of 35% aqueous acetonitrile which was previously cooled to −5° C. and 50 mL of water, and dried at 60° C. in vacuo to afford Compound 6 (8.74 g, 87.7%).

EXAMPLE 4

Synthesis of 2-(3-isoxazolyl)-3,6,7,9-tetrahydroimidazo[4,5-d]pyrano[4,3-b]pyridine

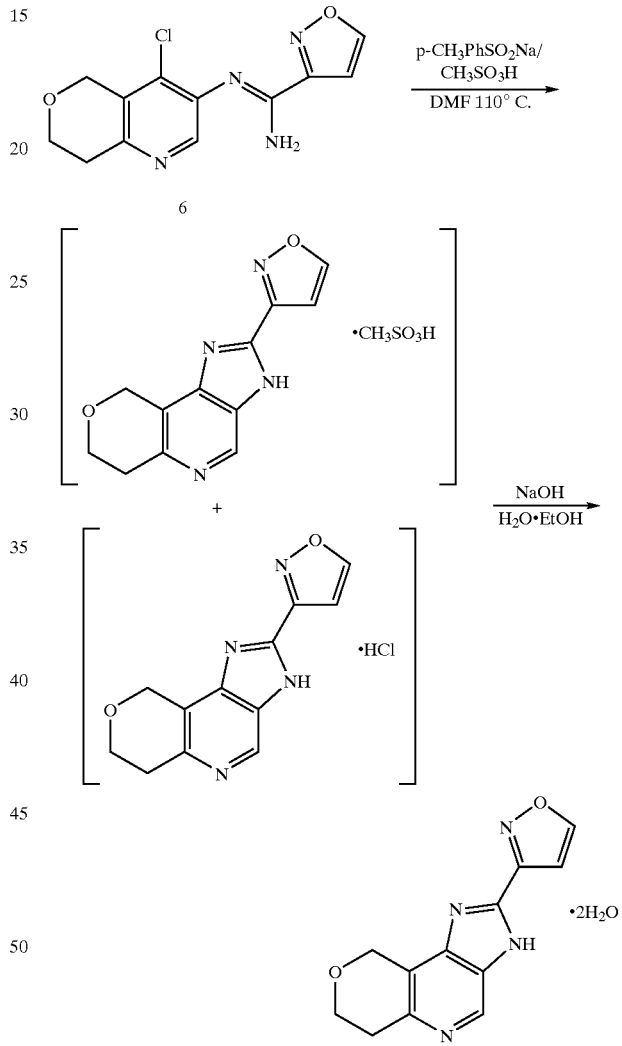

Compound 6 (1.25 g) was dissolved in 12 mL of dimethylformamide and 3.20 g of sodium p-toluenesulfinate was added. The solution was heated to 110° C. and 0.86 g of methanesulfonic acid was added. Solution of 3.75 g of Compound 6 in 12.5 mL of dimethylformamide was added dropwise over 1 hour at the same temperature. After the mixture was stirred for 1.5 hours at the same temperature and cooled, 40 mL of acetone was added to obtain a crude mixture salt (methanesulfonate and hydrochloride) of the titled compound.

Without drying, the obtained mixture salt was dissolved in 55.5 mL of water. 0.367 g of 96% sulfuric acid and 0.25 g of activated carbon were added and the mixture was stirred at 60° C. After cooling, activated carbon was filtered off, 41 mL of ethanol was added to the filtration and 18.5 g of 4.8% sodium hydroxide was added to neutralize. Precipitated crystals were filtered to obtain 3.99 g of free compound dihydrate of the title compound (80% yield).

EXAMPLE 5

Using a similar method of Example 4 except that the kind of sulfinate and existence or absence of acid, the desired compounds were synthesized and the effect of a sulfinate and acid was examined. The compound synthesized was 2-(3-isoxazolyl)-3,6,7,9-tetrahydroimidazo[4,5-d]pyrano[ 4,3-b] pyridine hydrochloride, which is described in JP 1993/286973 A. Number of mole equivalent in the following table means the volume per 1 mole equivalent of Compound 6 and "1V" means 1 mL per 1 g of Compound 6.

| Sulfunate | | Acid | | Solvent | Reaction temperature (° C.) | Reaction time (hr) | Yield (%) |
|---|---|---|---|---|---|---|---|
| Lithium p-toluene sulfinate | 1 mole equivalent | — | — | DMSO (2 V) | 145 | 1 | 92.0 |
| Lithium p-toluene sulfinate | 0.5 mole equivalent | — | — | DMSO (2 V) | 145 | 2 | 93.0 |
| Sodium p-toluene sulfinate | 0.5 mole equivalent | — | — | DMSO (2 V) | 145 | 2 | 90.5 |
| Sodium p-toluene sulfinate | 1 mole equivalent | Methane-sulfonic acid | 0.5 mole equivalent | NMP (4 V) | 94–97 | 1 | 90.4 |
| Sodium p-toluene sulfinate | 1 mole equivalent | Methane-sulfonic acid | 0.5 mole equivalent | NMP (4 V) | 94–97 | 2 | 94.0 |

NMP: N-methyl-2-pyrrolidone
DMSO: dimethylsulfoxide

REFERENCE EXAMPLE 1

Synthesis of 2-(3-isoxazolyl)-3,6,7,9-tetrahydroimidazo[4,5-d]pyrano[ 4,3-b]pyridine (free compound, dihydrate)

After Compound 6 (984 g, 3.53 mol) was added in a 5 L 4 necked flask equipped with a stirrer, a thermometer and a nitrogen gas tube, 1.97 L of N-methyl-2-pyrrolidone was poured therein to obtain a suspension. The suspension was reacted with stirring under mild nitrogen stream for 50 minutes at 190 to 210° C. (internal temperature) on oil bath at 200° C. After the reacted mixture was cooled to 40° C., 2 L of acetone was added to obtain a suspension. The obtained suspension was then transferred to a 20 L 4 necked flask, 7.84 L of acetone was added, and the mixture was cooled to 3° C. The precipitated crystals were filtered, washed twice with 1.3 L of acetone and air-dried for 18 hours to obtain 879 g of crude crystals of 2-(3-isoxazolyl)-3,6,7,9-tetrahydroimidazo[ 4,5-d]pyrano[4,3-b]pyridine (hydrochloride) (89.3%).

879 g of crude crystals were dissolved in 35.16 L of 20% aqueous isopropanol with heating and 505 mL of concentrated aqueous ammonia and 295 g of activated carbon were added. After the solution was heated to reflux for 20 minutes, activated carbon was filtered off, and the filtrate was washed sequentially with 6.7 L of warmed 20% aqueous isopropanol and 3.3 L of isopropanol. The filtrate and wash liquid were combined and concentrated under reduced pressure to obtain 9.95 kg of a concentrated solution. The obtained solution was cooled at 4° C. for 18 hours, precipitated crystals were filtered, washed twice with 1.8 L of ice-cooled 20% aqueous isopropanol and air-dried for 18 hours to obtain 764 g of the titled compound (77.8%).

mp >300° C.
Elemental Analysis ($C_{12}H_{10}N_4O_2.2H_2O$)
Calcd.: C,51.80; H,5.07; N,20.13; $H_2O$,12.95%
Found: C,51.85; H,5.10; N,20.30; $H_2O$,12.71%

EXAMPLE 6

Preparation of Needle Crystals

To 764 g of the compound (free compound, dihydrate) in a 30 L reaction vessel, 26.75 L of 20% aqueous isopropanol was added and dissolved with stirring under heating at 80 to 84° C. To this mixture, 76.4 g of activated carbon was added, and the mixture was stirred for 30 minutes at the same temperature. After the activated carbon was filtered off, the activated carbon was washed with 3.4 L of warmed 20% aqueous isopropanol. The filtrate and wash liquid were combined and transferred to a 60 L crystallizer. The solution was warmed to 78° C. to dissolve precipitated crystals, a solution of 389 g of 85% phosphoric acid (1.23 mol equivalent) in 389 mL of isopropanol was added, and the dropping vessel was washed with 400 mL of isopropanol. Though needle crystals were precipitated after one minute and the whole mixture was solidified, it turned to be a suspension by stirring at high speed. Thus obtained suspension was cooled to 4° C. and allowed to stand for 18 hours. After the suspension was took out from the crystallizer, the suspension was filtered and the residue was washed twice with 4.6 L of isopropanol and air-dried at room temperature for 18 hours to obtain 2-(3-isoxazolyl)-3,6,7,9-tetrahydroimidazo[ 4,5-d]pyrano[4,3-b]pyridine phosphate monohydrate (946.5 g, 96.2%) as needle crystals.

mp 234–236° C.
Elemental Analysis ($C_{12}H_{10}N_4O_2.H_3PO_4.H_2O$)
Calcd.: C,40.23; H,4.22; N,15.63; P,8.65; $H_2O$,5.03%
Found: C,40.39; H,4.17; N,15.92; P,8.53; $H_2O$,4.10%
Powder X-ray diffraction: 12.4, 14.7, 17.4, 19.6, 21.4, 25.0, 27.0 (degree)
IR: 3426, 3109, 1642, 1123, 998, 957 and 808 ($cm^{-1}$)

EXAMPLE 7

Preparation of Prism Crystals

To 3119 g of needle crystals (8.705 mol) obtained by the method of Example 6 in a 30 L reaction vessel equipped with a stirrer, 18.71 L of distilled water containing 50.18 g of 85% phosphoric acid (0.05 mol equivalent) was added to obtain a suspension. Crystalline nucleus already prepared was added thereto and stirred at room temperature (23 to 24° C.) for 43 hours. The precipitated crystals were filtered, washed twice with 1.5 L of ice-cooled distilled water and dried under reduced pressure at room temperature for 4 days to obtain 2902 g of 2-(3-isoxazolyl)-3,6,7,9-tetrahydroimidazo[ 4,5-d]pyrano[4,3-b]pyridine phosphate monohydrate as prism crystals (93.1%).

mp 167 to 170° C. (foam)
dp 242 to 252° C. (colored)
Elemental Analysis ($C_{12}H_{10}N_4O_2 \cdot H_3PO_4 \cdot H_2O$)
Calcd.: C,40.23; H,4.22; N,15.63; P,8.65; $H_2O$,5.03%
Found: C,40.25; H,4.26; N,15.71; P,8.64; $H_2O$,5.16%
Powder X-ray diffraction: 11.6, 15.3, 17.8, 20.9, 25.7, 26.2 and 27.9 (degree)
IR: 3264, 3104, 2533, 2085, 1648, 1119, 1089, 954 and 513 ($cm^{-1}$)

X-ray diffraction of 2-(3-isoxazolyl)-3,6,7,9-tetrahydroimidazo[4,5-d]pyrano[ 4,3-b]pyridine phosphate monohydrate in the above Examples, was detected under the following conditions.

X-ray diffraction conditions: Rigaku Corporation model RAD-C, powder X-ray diffraction meter, Target: Cu, Graphite Monochrometer, Tube voltage: 40 kV, Tube current: 40 mA, Slit: DS=0.5, RS=0/3, SS=0.1, Scan Speed: 3° /min, Detector Scintillation counter, Sample cell: small diameter, for small amount of samples (Φ 5 mm)

INDUSTRIAL APPLICABILITY

The process of the invention is capable of convenient and efficient production of amidine derivatives of the formula (II), which are intermediates of condensed imidazopyridine derivatives of the formula (I) that are useful for pharmaceuticals.

What is claimed is:

1. A process for producing a compound of the formula (II):

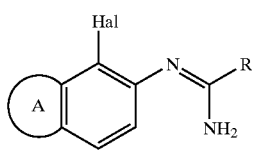

wherein
ring A represents a 5 to 9 membered alicyclic group, which may contain at least one of O, S, SO, $SO_2$ and/or $NR^1$ and may be substituted with at least one alkyl;
$R^1$ is hydrogen, alkyl, esterified carboxy, carbamoyl or acyl;
R is optionally substituted aryl or optionally substituted aromatic heterocyclic group; and
Hal is a halogen,
comprising
Step 1, wherein a compound of the formula (v):

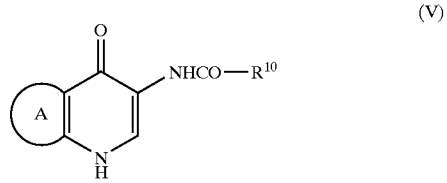

wherein
$R^{10}$ is optionally substituted aryl, optionally substituted aromatic heterocyclic group, optionally substituted alkyl, or optionally substituted cycloalkyl; and ring A is as defined above,
is reacted with a halogenating agent in acetonitrile in the presence of dimethylformamide and then hydrolyzed to obtain a compound of the formula (IV):

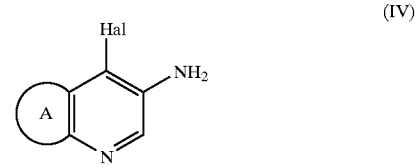

wherein ring A is as defined above, and Hal is a halogen,
Step 2, wherein the resultant compound (IV) is reacted with a compound of the formula $R—COR^{11}$, wherein R is optionally substituted aryl or optionally substituted aromatic heterocyclic group, and $R^{11}$ is hydroxy or halogen, in acetone in the presence of an organic base and optionally further a halogenating agent to obtain a compound of the formula (III):

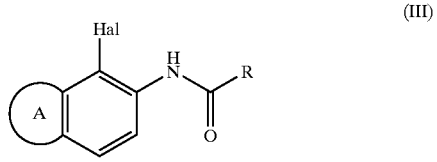

wherein ring A, Hal and R are as defined above, and
Step 3, wherein the obtained compound of the formula (III) is reacted with a halogenating agent in acetonitrile in the presence of an organic base and then aminated.

2. A process for producing a compound of the formula (IV):

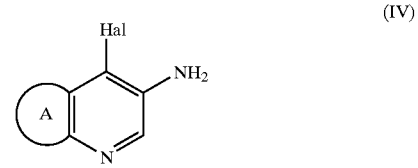

wherein
    ring A represents a 5 to 9 membered alicyclic group, which may contain at least one of O, S, SO, $SO_2$ and/or $NR^1$ and may be substituted with at least one alkyl; and
    $R^1$ is hydrogen, alkyl, esterified carboxy, carbamoyl or acyl;
    Hal is a halogen,
comprising that a compound of the formula (V):

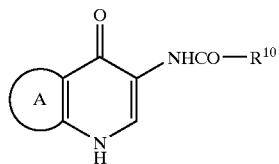
(V)

wherein
    $R^{10}$ is optionally substituted aryl, optionally substituted aromatic heterocyclic group, optionally substituted alkyl, or optionally substituted cycloalkyl; and ring A is as defined above,
is reacted with a halogenating agent in acetonitrile in the presence of dimethylformamide and then hydrolyzed.

3. A process for producing a compound of the formula (III):

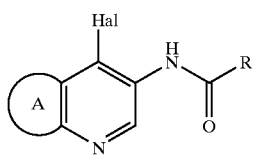
(III)

wherein
    ring A represents a 5 to 9 membered alicyclic group, which may contain at least one of O, S, SO, $SO_2$ and/or $NR^1$ and may be substituted with at least one alkyl;
    $R^1$ is hydrogen, alkyl, esterified carboxy, carbamoyl or acyl;
    R is optionally substituted aryl or optionally substituted aromatic heterocyclic group; and
    Hal is a halogen, comprising that a compound (IV):

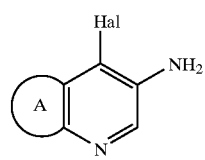
(IV)

wherein ring A, and Hal are as defined above, is reacted with a compound of the formula R-$COR^{11}$, wherein R is as defined above and $R^{11}$ is hydroxy or halogen, in the presence of an organic base and optionally further a halogenating agent.

4. A process for producing a compound of the formula (II):

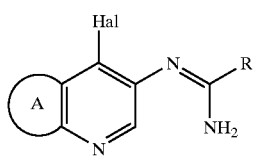
(II)

wherein
    ring A represents a 5 to 9 membered alicyclic group, which may contain at least one of O, S, SO, $SO_2$ and/or $NR^1$ and may be substituted with at least one alkyl;
    $R^1$ is hydrogen, alkyl, esterified carboxy, carbamoyl or acyl;
    R is optionally substituted aryl or optionally substituted aromatic heterocyclic group; and
    Hal is a halogen,
comprising that a compound of the formula (III):

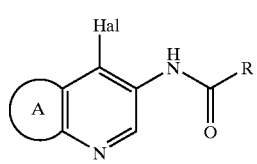
(III)

wherein ring A, R and Hal are as defined above, is reacted with a halogenating agent in acetonitrile in the presence of an organic base and then aminated.

5. A process for producing a compound of the formula (I):

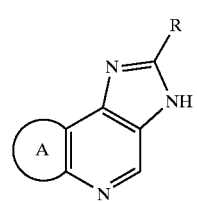
(I)

wherein
    ring A represents a 5 to 9 membered alicyclic group, which may contain at least one of O, S, SO, $SO_2$ and/or $NR^1$ and may be substituted with at least one alkyl;
    $R^1$ is hydrogen, alkyl, esterified carboxy, carbamoyl or acyl;
    R is optionally substituted aryl or optionally substituted aromatic heterocyclic group,
comprising
    Step 1, wherein a compound of the formula (V):

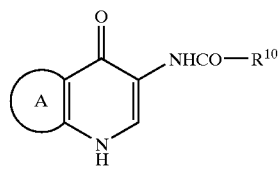
(V)

wherein

R[10] is optionally substituted aryl, optionally substituted aromatic heterocyclic group, optionally substituted alkyl, or optionally substituted cycloalkyl; and ring A is as defined above, is reacted with a halogenating agent in acetonitrile in the presence of dimethylformamide and then hydrolyzed to obtain a compound of the formula (IV):

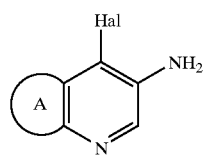

(IV)

wherein ring A is as defined above, and Hal is a halogen,

Step 2, wherein the compound (IV) obtained is reacted with a compound of the formula R—COR[11], wherein R is optionally substituted aryl or optionally substituted aromatic heterocyclic group, and R[11] is hydroxy or halogen, in the presence of an organic base and optionally a halogenating agent to obtain a compound of the formula (III):

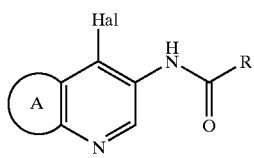

(III)

wherein ring A, Hal and R are as defined above,

Step 3, wherein the obtained compound of the formula (III) is reacted with a halogenating agent in acetonitrile in the presence of an organic base and then aminated to obtain a compound of the formula (II):

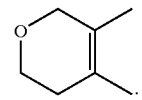

(II)

wherein ring A, Hal and R are as defined above, and

Step 4, wherein the obtained compound of the formula (II) is reacted in the presence of a sulfinate.

6. The process of any one of claims 1 to 5 wherein R is 3-isoxazolyl, and ring A is

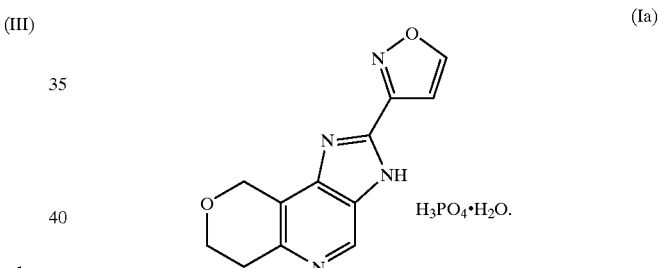

7. The process of claim 6, which further comprises a step wherein the obtained compound of the formula (I) is treated with an aqueous solvent containing phosphoric acid, and the obtained phosphate is crystallized by any conventional method to obtain 2-(3-isoxazolyl)-3,6,7,9-tetrahydroimidazo[4,5-d]pyrano[4,3-b]pyridine phosphate monohydrate of the formula (Ia):

(Ia)

$H_3PO_4 \cdot H_2O$.

* * * * *